(12) United States Patent
Niazi

(10) Patent No.: US 6,419,963 B1
(45) Date of Patent: Jul. 16, 2002

(54) COMPOSITION AND METHOD FOR THE TREATMENT OF DIAPER RASH USING NATURAL PRODUCTS

(76) Inventor: Sarfaraz K Niazi, 20 Riverside Dr., Deerfield, IL (US) 60015

( * ) Notice: Subject to any disclaimer, the term of this patent is extended or adjusted under 35 U.S.C. 154(b) by 0 days.

(21) Appl. No.: 09/681,520

(22) Filed: Apr. 22, 2001

(51) Int. Cl.$^7$ ................................................. A61K 35/78
(52) U.S. Cl. ........................ 424/757; 424/725; 424/539; 514/26
(58) Field of Search ................................ 424/539, 725, 424/757; 514/26

(56) References Cited

U.S. PATENT DOCUMENTS

| | | | |
|---|---|---|---|
| 4,101,652 A | * | 7/1978 | Bonati |
| 5,110,593 A | * | 5/1992 | Benford |
| 5,371,245 A | * | 12/1994 | Rindone et al. |
| 5,618,529 A | * | 4/1997 | Pichierri |

OTHER PUBLICATIONS

Caplus English abstract of Chinese Patent No. 1113109 A (12–1995).*

* cited by examiner

Primary Examiner—Leon B. Lankford, Jr.
Assistant Examiner—Susan D. Coe
(74) Attorney, Agent, or Firm—Welsh & Katz, Ltd.

(57) ABSTRACT

Provided here is a pharmaceutical composition containing beeswax, olive oil, β-sitosterol and the herb Coptis chinesis Franch for safe and quick treatment for infant and adult diaper rash. Also provided here is a methodology for the treatment of diaper rash wherein the treatment consists of compositions that contain naturally derived anti-inflammatory agents, an antimicrobial agents and such components that they provide an occlusive coating when applied to the afflicted surface.

10 Claims, No Drawings

COMPOSITION AND METHOD FOR THE TREATMENT OF DIAPER RASH USING NATURAL PRODUCTS

BACKGROUND OF INVENTION

Diaper rash is a common form of irritation and inflammation of those parts of an infant's or adult's body normally covered by a diaper. It frequently occurs also in areas immediately adjacent to the diapered area. This condition is also referred to as diaper dermatitis, napkin dermatitis, napkin rash, and nappy rash.

The precise number of infants who suffer from diaper rash or diaper dermatitis is unknown. However, the United States Department of Health, Education and Welfare, has indicated that diaper dermatitis itself accounted for 97 visits to a doctor for every 1,000 infants in the United States between the ages of 0 to 2 years of age. [See Ambulatory Care Utilization Patterns of Children and Young Adults, Vital and Health Statistics Series 13, Number 39, U.S. Department of Health, Education and Welfare, Public Health Service (1978)]. Further, while certainly more common in infants, this condition is not, in fact, limited to infants. Any individual who suffers from incontinence may develop this condition. This ranges from newborns, to the elderly, to critically ill or non-ambulatory individuals. Approximately 10% of all infants can have their diaper rash classified as being moderate, with another 5% of the infants having diaper rash, which could be classified as severe.

The primary contributors to the development of diaper rash have long been thought to be infant urine and feces. For example, infants under two months of age can urinate up to 20 times per day. Thereafter, infants can urinate up to 8 times a day. In addition, infant defecation typically occurs several times a day.

The principal cause of the irritation that characterizes diaper dermatitis or diaper rash is the mixture of urine and stools. In effect, the urea contained in the urine is broken down into ammonium hydroxide by the ureases, which leads to an increase in pH. When the pH becomes basic, the enzymes produced at time of digestion such as the proteases and the lipases of pancreatic or intestinal origin, see their activity and thus their irritating power increase. The lipases in particular attack the triglycerides of the sebum and provoke the release of fatty acids.

The corium made permeable by a hyper-hydration, a significant rubbing and digestion by enzymes loses its function as a barrier and allows other irritating molecules such as biliary salts to pass through. In certain cases, an actual digestion of the epidermis of the infant's bottom could be observed due to the action of ureases, lipases and proteases.

It had been theorized that the breakdown of the urine to yield ammonia primarily contributed to the formation of diaper rash by increasing the alkalinity of the skin. However, more recent studies have concluded that the primary contributor to the development of diaper rash is the feces. As opposed to the alkaline pH associated with urine, feces typically exhibit an acidic pH due to bile. In fact, studies have shown that diaper rash is more prominent in the presence of feces than in the presence of urine, thereby providing a plausible explanation for the problems with diaper rash associated with infants who have diarrhea or frequent stools.

Diaper rash may predispose an infant to irritation and infection. It is generally accepted that true "diaper rash" or "diaper dermatitis" is a condition, which is, in its most simple stages, a contact irritant dermatitis [See Jacobs, "Eruptions in the Diaper Area", Ped. Clin North Am 25:209 (1978)]. The irritation of simple diaper rash results from extended contact of the skin with urine, or feces, or both. Diapers are worn to catch and hold the body waste, but generally hold the waste in direct contact with the skin until changed, i.e., in occluded fashion for long periods of time. The same is true for an incontinence pad, or incontinence brief. However, while it is known that body waste "causes" diaper rash, the precise component or components of the urine or feces which are responsible for the resulting irritation of the skin remain the subject of much controversy. The most commonly accepted list of factors linked to diaper rash includes ammonia, bacteria, and the products of bacteria action, urine pH, and moisture. These are generally cited in the art as being the most likely candidates. The two most common types of infection are those associated with yeast, and bacteria. The most common yeast infection is caused by Candida albicans. Meanwhile, the most common bacterial infection is caused by Staphylococcus aureus.

There are a host of conditions, which are labeled (or more precisely mislabeled) "diaper rash" which may exhibit similar indications. In determining whether the condition that is being observed is actually diaper rash/dermatitis or some other condition no conclusive rule exists. If the dermatitis is limited to the diapered area and related to the use of the diaper or the contact of skin to body waste it can be safely concluded that the condition that exists is diaper dermatitis. There are a number of other conditions, however, which can begin in the area that is diapered on the infant, or which are simply more pronounced or aggravated in this area, but which are not truly "diaper rash" or "diaper dermatitis" in that they are not related to body waste contact. If the abnormal skin condition under scrutiny is present in locations other than in, or proximate to, the diapered area, e.g., the head, neck, extremities other than the genitalia, shoulders, etc., then one must consider other conditions, such as atopic dermatitis, seborrheic dermatitis, allergic contact dermatitis, psoriasis, scabies, bullous impetigo, papular urticaria, herpes simplex, and chemical or thermal burns. However, such observations are not conclusive because some diaper rash or diaper dermatitis conditions may have their genesis in the diapered area and then spread well beyond the diapered area.

Weston, et al., "Diaper Dermatitis: Current Concepts", Pediatrics 66:4 (1980) has described and summarized the overall clinical features which can generally be associated with true diaper dermatitis. He has identified the forms of diaper rash or diaper dermatitis as follows: Four clinical forms of diaper dermatitis related to diaper wear have been recognized. The most frequently observed is chafing dermatitis. This form demonstrates mild redness and scaliness seen over the buttocks, waist, and convex surface of the thighs where the diaper contacts the skin, or limited to the perianal area. Dermatitis limited to the perianal area is seen in the neonatal period, and the more widespread form is seen after 3 months of age. The second, and also frequently seen, form of dermatitis is a sharply demarcated confluent erythema with involvement of the skin folds with or without an accompanying whitish exudate. The third form of dermatitis is characterized by discrete shallow ulcerations scattered throughout the diaper area including the genitalia. In the fourth form, beefy red confluent erythema of the entire perineum with prominent elevated margins, satellite oval lesions around the periphery of the confluent area, and vesiculopustular lesions are described. This form is seen when the dermatitis becomes secondarily invaded with Candida albicans. Diffuse involvement of the genitalia in the inguinal folds is a regular feature of this form. If left untreated, diaper rash and diaper dermatitis can result in masceration of the skin, thus leading to much more serious conditions and pathologies, e.g., infection, trauma, and systemic disease. [See Burgoon, "Diaper Dermatitis", Pediatric Clinics of North America 18:835 (1961)].

Since a diverse range of factors have been suspected of being associated with diaper rash and diaper dermatitis requiring diverse therapies, conventional methods of treatment for diaper dermatitis have been directed toward a straightforward attempt to minimize the contact of the skin with the feces or urine present in a soiled diaper. An artificial barrier is usually provided between the skin and the body waste to accomplish this. There have also been further attempts directed toward counteracting other suspected causes of diaper rash by promoting dryness in the diapered area, and preventing microbial growth and inflammation with conventional agents. Such a strategy would include frequent diaper changing, reduced use of plastic pants, triple diapering, careful washing and sterilization of diapers, treatment with an anti-Candidal agent, reduction of inflammation (by application of a topical application of a low potency glucocorticoid steroid), and the possible use of a bacteriostatic agent as a prophylactic measure in the diaper rinse. However, because the exact components of urine or feces which act as factors or cofactors contributing to diaper dermatitis have never been precisely identified, the most effective method of treating diaper dermatitis to date has been the artificial barrier. This had led to the frequent use of an occlusive, barrier-type topical, such as petrolatum or zinc oxide, to provide this protection, preventing the unknown offending component from coming in contact with the skin.

To combat diaper rash, the means used in current therapy such as supervision of the infant's diet and the type of diaper used and ensuring good hygiene and the application of standard barrier creams are not judged satisfactory by a large number of dermatologists and pediatricians. Currently available treatments for diaper rash are generally based upon the use of zinc oxide, vitamins (A, D, and D3), or some combination thereof. These active ingredients are incorporated into a cream or salve by blending them into various purified semisolid ointment bases, e.g. mineral oil, petrolatum, soft paraffin, lanolin, and the like. While these treatments are often times effective for treating routine, simple diaper rashes, severe cases of diaper rash, especially those often observed with incontinent adults, have proved resistant to the treatments.

Most of the diaper rash products currently available are in the form of an ointment or a water-in-oil emulsion. The high viscosity associated with these products keeps the diaper rash product from being washed away by urine or feces. In many cases, the high viscosity is the result of the inclusion of zinc oxide. Thus, the typical anhydrous, hydrophobic ointment prevents urine or feces from coming into direct contact with the skin by their being repelled from the ointment surface. As such, the product acts as a barrier, inhibiting any penetration into the diaper rash product by any liquid.

Pertinent prior art includes U.S. Pat. No. 1,809,082, soap, perfumery and cosmetics. For example, Desitin® ointment is probably the most common topical used in treating diaper rash. It contains both of the common barrier materials (zinc oxide and petrolatum) and additionally contains two common skin-conditioning agents (cod liver oil and lanolin). All of these agents are commonly used in topical skin conditioning preparations.

Petrolatums, as well as zinc oxide, are well known to be highly effective barrier materials. Zinc oxide is also known to be effective when applied externally as a mild astringent for the skin, as a barrier material to prevent eczema, and also as a barrier protective to slight excoriations. It has been used in pastes and creams in combination with many other topical actives. [See Martindale, The Extra Pharmacopoeia, 26th Ed., p. 585, The Pharmaceutical Press (1975)]. Zinc oxide is almost totally insoluble in water. Petrolatum (petroleum jelly; paraffin jelly; vasoliment; Vaseline®) is commonly used as an occlusive barrier material in topical preparations. Petrolatum is a purified mixture of semi-solid hydrocarbons of the general formula $C_nH_{2n+2}$, when n is about 16 to about 32. Premium petrolatum is a white, semi-solid, unctious mass which is odorless and tasteless.

Zinc glycerolate (the reaction product of zinc oxide and glycerine) is cited as being useful as a topical treatment for skin disorders, including ammoniacal dermatitis in babies in PCT Application 8201-867. This disclosure indicates that the "zinc glycerolate" complex is insoluble in water. [See also PCT Application 8201-867].

Zinc chloride is known as a powerful caustic and astringent. Its known uses include incorporation within mouthwashes, eye drops, and as deodorizer for foul smelling wounds and ulcers. See Martindale, The Extra Pharmacopoeia, 62th Ed., p. 270, The Pharmaceutical Press (1975).

U.S. Pat. No. 4,349,536, Hausler, issued Sep. 14, 1982, describes the use of zinc (II) and copper (II) trace minerals in a cream base to promote sun-tanning.

U.S. Pat. No. 4,160,820, Sipos, issued Jul. 10, 1979, indicates that a glycerine solution containing about 0.5% to about 8% of a glycerine-soluble zinc salt is useful in the treatment of gingivitis when applied topically to the gums.

U.S. Pat. No. 3,996,346, Staffier, et al., issued Dec. 7, 1976, indicates that a combination of zinc oxide and zinc phenate is useful as a deodorant and an anti-perspirant when applied topically to the underarm area or the feet.

U.S. Pat. No. 3,964,486, Blaney, issued Jun. 22, 1976, describes a disposable diaper or pad comprising an absorbent substrate having incorporated therein adipic acid in a quantity sufficient to inhibit ammonia formation and concomitant diaper rash. It describes the use of adipic acid in the diaper at a level sufficient to provide the urine with a pH in the range of about 3.5 to about 5.5 during use throughout the entire diaper upon wetting with urine.

A copper sulfate/zinc sulfate combination is useful as a wet dressing in the treatment of eczema and impetigo in addition to being useful as a local astringent for eye infections. [Martindale, The Extra Pharmacopoeia, 26th Ed., p. 475, The Pharmaceutical Press (1975)].

Soluble metallic salts, particularly zinc, silver and lead ions, are known as lipase inhibitors. [See Lowenstein, Methods in Enzymology, Vol. XIV, p.176, Academic Press, (1969)].

It is also known that the salts of copper are useful in topicals, astringents and fungicides. [Martindale, The Extra Pharmacopoeia, 26th Ed., p. 473–475, The Pharmaceutical Press, (1975)].

Polyethylene glycols (PEGs) are polymers produced by the reaction of ethylene oxide with ethylene glycol or water. PEGs with molecular weights up to about 600 are liquids at room temperature and they closely resemble highly refined petrolatum/mineral oils in appearance and consistency. They are widely used as ointment bases for water-soluble agents.

[Goodman, et al., The Pharmacological Basis of Therapeutics, 5th Ed., p. 946–947, Macmillan Publishing Co. (1975)].

Polyethylene glycol ointment, U.S.P., PEG 300, NF, PEG 400, U.S.P., PEG 600, U.S.P., are all listed in the cited official compendia. PEGs are known as agents with the ability to provide mechanical occlusive protection from dermal irritants. [jellinik, Formulation and Function in Cosmetics, p. 322, Wiley—lnterscience, New York (1970)].

The use of a 50:50, by weight, mixture of PEG 400:PEG 4000 as a topical vehicle for a water-soluble active is well known. [anker, et al., Modern Pharmaceutics, Marcel Dekker, P. 310 (1979)].

Triacetin, (1,2,3-propanetriol triacetate), is a colorless, oily liquid which is known as a topical anti-fungal. [The Merck Index, 9th Ed., p. 1232, Merck and Co. (1976)]. The "self-regulating" action of triacetin (Enzactin.®) is known, i.e., it is known that at the neutral (or higher) pH of the affected skin, glycerol and free fatty acid (acetic acid) are rapidly liberated from triacetin as a result of the action of the esterase enzymes found abundantly in skin, serum, and fungi. The growth of the fungi is inhibited by the free fatty acid IGlyceol esters are known to be enzyme substrates, which, when acted upon by a hydrolyzing enzyme, will be hydrolyzed resulting in the release of free fatty acids.

An example of a diaper rash product is British Patent No. 1,357,731. That patent discloses a unique powder composition, which can be incorporated into a hydrophobic ointment. A buffer system is provided to buffer the composition at a pH of from 5.5 to 7.5, and preferably from 6 to 7. That patent discloses that a citric acid/sodium citrate buffering system does not have superior buffering capacity when compared with other buffering systems.

Another example of the prior art is U.S. Pat. No. 4,556,560 issued to Buckingham. This patent discloses and claims use of lipase inhibiting agents, such as the water soluble metallic salts including zinc chloride, in the treatment of diaper rash. This patent purports to treat diaper rash by inhibiting the deleterious effects of the enzyme lipase action on the skin, said inhibition being achieved by incorporating a inhibitory agent of said lipase action into a barrier like carrier, said carrier having the characteristics of being relatively hydrophobic in nature thereby forming an effective barrier to the skin against urine and feces.

Yet another example of the prior art is U.S. Pat. No. 4,996,238 issued to Matravers. This patent discloses and claims a skin protective composition exhibiting enhanced water repellency and skin conditioning effects and contains aliphatic waxes and hydrophobic silicones. Matravers sspecifically iscloses and claims the use of an admixture consisting of a fatty acid admixed with one or more hydrophobic silicones.

Another example of the prior art is U.S. Pat. No. 4,904,524 issued to Yoh. This patent discloses and claims the encapsulation and micro-bead formation and use thereof of the active silicon agent (Dimethicone) in the preparation of cloth wipes in the treatment of diaper rash. This patent specifically discloses the need for an elevated concentration of encapsulated beads containing the active agent at the surface of the wipe. The stability, presence and delivery of the active agent within the wipe is directly linked to, and dependent on the process used to form and adhere the encapsulated beads to the paper wipe.

Other studies, such as one published in The Practitioner, Vol 210:824–828 (1973), discuss a boric acid/borax buffer system for use as a diaper rash product.

However, studies conducted during the 1970's brought about concerns of boron toxicity such that products containing boric acid had to be reformulated thereby eliminating boric acid as an ingredient.

Still another approach to products containing anhydrous, hydrophobic zinc oxide was the incorporation into such products of alkoxylated ether/esters Such as polypropyleneglycol myristyl ether propionate. Although this approach rendered the diaper rash products less greasy, it did not completely resolve the problem associated with the zinc oxide content.

The U.S. Pat. Nos. 6.051,749 and 5,869,033 to Schulz are for a fabric or garment containing fecal enzyme inhibitor. Inactivating the fecal proteolytic enzymes by contact with organophilic clays prevents skin irritation, such as diaper rash, appearing when the skin is allowed to remain in contact with proteolytic enzymes found in feces. The organophilic clays are applied to the skin in areas likely to come into contact with feces or to garments such as diapers. A composition suitable for practicing the method of the invention comprises an amount of organophilic clay effective to inactivate irritating fecal proteolytic enzymes dispersed in a pharmaceutically acceptable non-toxic dermatological vehicle. A fabric incorporating organophilic clay, preferably dispersed in a matrix of a super-absorbent polymer is useful for preparing diapers for infants that can help to prevent skin irritation by fecal enzymes.

The U.S. Pat. No. 5,618,529 to Pichierri is for an improved method of treating diaper rash in both infants and adults is described. The method entails coating the affected area with a composition containing a copolymer of lower alkyl vinyl ether and maleic acid, or a derivative of the copolymer.

The U.S. Pat. No. 5,436,007 to Hartung, et al., is for a skin lotion containing a linear polydimethylsiloxane polymer, a non-ionic emulsifier, consisting of polyoxyethylene sorbitan fatty acid esters, sorbitan fatty acid esters, polyoxyethylene alcohols, or polyoxyethylene fatty ethers aloe vera, an alkoxylated ether/ester, sodium citrate, citric acid, a blend of propylene glycol, diazolidinyl urea, methyl paraben and propyl paraben, and water. Most preferably the buffering system results in the lotion having a pH of about 5.2, which neutralizes acidic and basic by-products of urine and fecal matter. The lotion has a preferred viscosity in the range of 10–20,000 centipoise. The lotion is easily washed off with soap and water and is useful in the protection and treatment of diaper rash.

he U.S. Pat No.5,194,261 to Pichierri is an improved method of treating diaper rash in both infants and adults is described. The method entails coating the affected area with a composition containing a copolymer of lower alkyl vinyl ether and maleic acid, or a derivative of the copolymer.

The U.S. Pat. No. 5,091,193 to Enjolras, et al., is for a composition for preventing or treating diaper rash comprising an effective amount of zinc oxide and at least one antienzyme sufficient to treat or prevent diaper rash and an inert pharmaceutical carrier and a method of treating or preventing diaper rash on newborn babies.

The U.S. Pat. No. 4,816,254 to Moss is an invention that provides an ointment composition for treating skin irritations such as diaper rash and decubitus. The composition includes zinc oxide, boric acid, karaya gum, peruvian balsam, cod liver oil and an appropriate solvent and pharmaceutical carrier.

The U.S. Pat. No. 5,728,391 to lkeya, et al., is for an agent for treating a skin disease selected from the group consisting of a contact dermatitis treating agent, a xerosis senilis treating agent, an asteatosis treating agent, a housewives eczema treating agent, a keratosis treating agent, an eczema chronicum treating agent, a miliaria treating agent and a diaper rash treating agent, which contains hyaluronic acid and/or its salt having an average molecular weight of from 800,000 to 4,000,000, as an active ingredient.

The U.S. Pat. No. 5,538,740 to Abad is for an active ingredient for a therapeutic or cosmetic composition is obtained from live gastropoda (e.g., snails), which are physically stimulated (e.g., by centrifuging) to cause secretion of a fluid, which is then centrifuged and filtered. Preferably the gastropoda are fasted prior to the physical stimulation. The therapeutic or cosmetic compositions contain about 0.1–30% of the active ingredient which is a mixture of amino acids and nontoxic substances, an effective amount of an excipient preferred for use with biologically active ingredients, and other conventional ingredients provided they do not affect the stability and/or the activity. The therapeutic composition, in the form of a topical cream, can be used to treat various types of burns, dermatitis, eczema, diaper rash, and difficult to heal wounds. It can also be used to prevent skin cancer and radiodermatitis. The cosmetic composition can be used as hand and face creams, an anti-wrinkle cream, a sunscreen cream, a moisturizing lotion, and a deodorant.

The U.S. Pat. No. 5,762,945 to Ashley is for a topical composition for the treatment of the symptoms of diaper rash is disclosed comprising the combination of equal rations of nystatin powder, zinc oxide, and Aquaphor™, and mixed with a larger volume of U.S.P. cold cream.

DETAILED DESCRIPTION

In this invention, we have discovered that the ideal treatment for diaper rash is to provide a combination of components that have diversified activity. We have found that the natural composition described below provides an optimal and safe modality for the treatment of all types of diaper rashes as defined and described above.

A typical formulation of our invention includes all natural ingredients. It contains 2–20% beeswax, olive oil, soybean oil extract for0.1–50% β-sitosterol and 1–50% of the herb Coptis chinensis Franch. A preferred embodiment includes the following composition: Coptis chinensis Franch, 5% (as an extract) β-sitosterol 0.5% (from soybean extract), Beeswax 8%, Olive Oil qs.

Coptis chinensis Franch used in the invention is selected but not limited to one or more from the group of Coptis deltoidea C. Y. Cheng et Hsiao, Coptis omeiensis (Chen) C. Y. Cheng, and Coptis teetoides C. Y. Cheng of Ranunculaceae Family. The root is used. (A Dictionary of Chinese Materia Medica, Shanghai Science and Technology Press, 1988, pages 2022 to 2030). The primary components include: berberine, coptisine, worenine, palamtine, jatrorrhizine, epiberberine, magnoflorine, and columbamine. It has a very broad spectrum antibacterial property against gram-positive and gram-negative pathogens such as alpha and beta hemolytic streptococci, *staphylococcus aureus, virbio cholerae, diplococcus intracellularis, diplococcus pneumoniae, bacillus anthracis, bacillus tetani, diptheria bacillus, tuberculosis bacillus, E coli*. It also inhibits leptospira. A remarkable effect of huanglian is that it enhances the phagocytic activities of leukocytes and liver reticuloendothelial system. It also acts as vasodilator.

A large volume of scientific literature establishes the safe antibacterial and other pharmacological properties of Coptis chinensis Franch as shown below.

Qin C L, Liu J Y, Cheng Z M: Pharmacological studies on the effects of huanglian decoction on experimental gastric lesions in rats and antiemetic in pigeons. Chung Kuo Chung Yao Tsa Chih July 1994; 19(7):427–30, 448. The results showed that Huanglian decoction has protective effect on ethanol-, HCl- and aspirin-induced gastric hemorrhagic lesions in rats and antemetic effect on CuSO4-induced vomiting in pigeons. A dose of 27 g/(kg.d) po applied in mice showed no toxic action. This dose is 400 times that of clinical application.

Franzblau SG, Cross C: Comparative in vitro antimicrobial activity of Chinese medicinal herbs.J Ethnopharmacol March 1986; 15(3): 279–88. Eighteen herbs used in the treatment of infectious diseases in traditional Chinese medicine were evaluated for in vitro activity against ten microbial pathogens. Lyophilized teas were tested by the agar dilution technique at 100–1600 micrograms/ml. Eleven of the preparations were active against at least one microorganism and six of these were active against at least three of the test isolates. Huangqin (Scutellaria sp.) and Huanglian (Coptis sp.) were each active against five of the isolates. Huangqin inhibited *Klebsiella pneumoniae* and *Proteus vulgaris* at 200 micrograms/ml. Huangqin alone showed strong activity against *Mycobacterium smegmatis* (less than or equal to 100 micrograms/ml) and *Candida albicans* (200 micrograms/ml). The antimicrobial activity of various teas, prepared with equal weights of herbs, could be compared against a particular pathogen by considering both the percentage of water-soluble material in the herbs and the minimum inhibitory concentrations of the filtered, lyophilized decoctions.

The choice of Coptis chinensis is made here as a potent antimicrobial agent. It does not contain any antibiotics to which patients can get resistant to, nor does it contain any irritating chemicals that might exacerbate the inflammation of skin. There are, however, other naturally derived components that possess antimicrobial activity against the type of organisms that infect during the formation of diaper rash. These may be substituted for Coptis chinensis. One may also use a combination of such herbs.

The major pharmacological effects of β-sitosterol are anti-inflammation, antiulcer, promotion of injured tissue and as we have demonstrated, stimulation of basal dermal stem cell cells. Soybean extract containing a minimum of 40% β-sitosterol as used in this invention (Sigma Chemicals Catalog S5753), which also contains campesterol, dihydrobrassicacasterol prepared according to the method of N. Kozumi, et al., Chem. Pharm. Bull., 27: 38, 1979. The source of β-sitosterol however is not relevant. It could be obtained from natural sources or from synthetic sources. β-sitosterol ($C_{29}H_{50}O$, molecular weight 414.72) is a common sterol in plants. It is generally isolated from wheat germ, soybean or corn oil. Sterols are important cyclized triterpenoids that perform many critical functions in cells. Phytosterols such as campesterol, stigmasterol and β-sitosterol in plants, ergosterol in fungi and cholesterol in animals are each primary components of the cellular and sub-cellular membranes in their respective cell types. The dietary source of phytosterols in humans comes from vegetables and plant oils. The estimated daily phytosterol content in the conventional western-type diet is approximately 250 mg in contrast to a vegetable diet, which would provide double that amount. Although having no nutritional value to humans, phytosterols have recently received a great deal of attention due to their possible anti-cancer properties and their ability to decrease cholesterol levels when fed to a number of mammalian species, including humans. Phytosterols aid in limiting cholesterol absorption, enhance biliary cholesterol excretion and shift cholesterol from atherosclerotic plaque. While many of the mechanisms of action remain unknown, the relationship between cholesterol and phytosterols is apparent. This is perhaps not surprising given that chemically, phytosterols closely resemble cholesterol in structure. The major phytosterols are β-sitosterol, campesterol and stigmasterol. Others include stigmastanol (β-sitostanol), sitostanol, desmosterol, chalinasterol, poriferasterol, clionasterol and brassicasterol. (Gould R. G., Jones R. J., LeRoyu G. V., Wissler R. W., Taylor C. B.; Absorbability of β-sitosterol in humans; Metabolism, (August) 1969;18 (8): 652–662; Tabata T., Tanaka M., Lio T.; Hypocholesterolemic activity of phytosterol. II; Yakugaku Zasshi, 1980;100 (5): 546–552. Hepistall R. H., Porter K. A.; The effect of β-sitosterol on cholesterol-induced atheroma in rabbits with high blood pressure; Br. J. Experimental Pathology, 1957;38: 49–54.) Several novel applications of phytosterols including β-sitosterol have been reported. The U.S. Pat. No. 5,965,449 to Novak describes a method of assessing risk for cardiovascular disease and other disorders and phytosterol-based compositions useful in preventing and treating cardiovascular disease and other disorders. The level of serum campesterol and β-sitosterol are determined and their ratio is correlated with the risk of cardiovascular or a related disorder. The U.S. Pat. No. 5,523,087 to Shlyankevich is for a pharmaceutical composition for the treatment of diabetic male sexual dysfunction; it contains physosterogens, phosphatidyl choline, β-sitosterol, Damiana leaf extract and vitamins and minerals. The U.S. Pat. No. 5,486,510 to Bouic, et al., is for a mixture of β-sitosterol glucoside and β-sitosterol is administered to persons for the modulation or control of immune responses. The U.S. Pat. No. 5,747,464 to See is for a composition for inhibiting absorption of fat and cholesterol from the gut and a method for making and using the composition. The composition comprises β-sitosterol bound irreversibly to pectin to form a β-sitosterol and pectin complex. The U.S. Pat. No. 5,118,671 to Bombardelli, et al., is for complexes formed between aescin, cholesterol or β-sitosterol and phospholipids and a method for producing an anti-inflammatory effect is also described.

Natural beeswax contains many still yet unidentified components that have for centuries provided healing properties for many ailments. Propolis is just one such example. The isolation of D-002 series of alcohols provides the clue to its anti-inflammatory activity; flavolins and other minor components provide impart many pharmacologic properties to beeswax. In addition to its chemical and pharmacological characteristics, the natural crystalline structure of beeswax allows formation of a matrix structure when mixed with vegetable oils in specific proportions that further act to remove skin debris.

A large volume of published data attests to the therapeutic activity of beeswax.

Carbajal D, Molina V, Valdes S, Arruzazabala M L, Mas R, Magraner J: Anti-inflammatory activity of D-002: an active product isolated from beeswax.

Prostaglandins Leukot Essent Fatty Acids October 1998; 59 (4): 235-8. D-002 is a natural mixture of high molecular weight alcohols isolated and purified from beeswax, which contains triacontanol among its main components. This study was undertaken to investigate the anti-inflammatory effects of D-002 administered by the oral route in two animal models commonly used in the pharmacological screening of anti-inflammatory drugs. D-002 administered orally to rats (100 and 200 mg/kg) produced a mild but significant reduction of exudate volume in carrageenan-induced pleuritic inflammation that was accompanied by a marked and significant decrease of leukotriene B4 (LTB4) levels in the exudate. D-002 (25, 50 and 200 mg/kg) also significantly diminished the granuloma weight in the cotton pellet granuloma in rats. In both cases, D-002 was less effective than indomethacin, which was used as an established anti-inflammatory reference drug. On the other hand, D-002 administered from 25–1000 mg/kg did not induce erosions or gastromucosal lesions in rats, which differs from results usually obtained with non-steroidal anti-inflammatory drugs. These results indicate that D-002 is a mild anti-inflammatory agent without any ulcerogenic effect associated. The results suggest that these effects are probably not mediated through an inhibition of cyclooxygenase, but a reduction in LTB4 levels induced by D-002 could explain these results.

Carbajal D, Molina V, Valdes S, Arruzazabala L, Mas R: Anti-ulcer activity of higher primary alcohols of beeswax. J Pharm Pharmacol September 1995; 47 (9): 731–3. The anti-ulcer effects of a natural mixture of higher aliphatic primary alcohols, designated D-002, isolated from beeswax, were compared with those of cimetidine on indomethacin-, ethanol-, water-immersion-induced ulcers and on gastric secretion in rats. D-002 (25–50 mg kg-1 p.o.) was similar to cimetidine in dose-dependently reducing the duration of indomethacin-induced ulcers while also being effective in preventing ethanol-induced ulcers, which are not affected by cimetidine. On the other hand, D-002 (100 mg kg-1) moderately decreased the volume of gastric basal secretion in pylorus-ligated rats, but not the acidity. Nevertheless, it inhibited gastric ulcer induced by pylorus-ligation at doses (50 mg kg-1) that were ineffective in decreasing the volume. In addition, 100 mg kg-1 of D-002 prevented the formation of acute gastric ulcers induced in rats by water-immersion stress. The results demonstrate the anti-ulcer activity of the preparation in different experimental models suggesting its potential value for ulcer therapy.

Carbajal D, Molina V, Valdes S, Arruzazabala M L, Mas R, Magraner J: Anti-inflammatory activity of D-002: an active product isolated from beeswax.Prostaglandins Leukot Essent Fatty Acids October 1998;59(4):235–8. D-002 is a natural mixture of high molecular weight alcohols isolated and purified from beeswax, which contains triacontanol among its main components. This study was undertaken to investigate the anti-inflammatory effects of D-002 administered by the oral route in two animal models commonly used in the pharmacological screening of anti-inflammatory drugs. D-002 administered orally to rats (100 and 200 mg/kg) produced a mild but significant reduction of exudate volume in carrageenan-induced pleuritic inflammation that was accompanied by a marked and significant decrease of leukotriene B4 (LTB4) levels in the exudate. D-002 (25, 50 and 200 mg/kg) also significantly diminished the granuloma weight in the cotton pellet granuloma in rats. In both cases, D-002 was less effective than indomethacin, which was used as an established anti-inflammatory reference drug. On the other hand, D-002 administered from 25–1000 mg/kg did not induce erosions or gastromucosal lesions in rats, which differs from results usually obtained with non-steroidal anti-inflammatory drugs. These results indicate that D-002 is a mild anti-inflammatory agent without any ulcerogenic effect associated. The results suggest that these effects are probably not mediated through an inhibition of cyclooxygenase, but a reduction in LTB4 levels induced by D-002 could explain these results.

Liu F, Sun D: Active constituents lowering blood-lipid in beeswax. Zhongguo Zhong Yao Za Zhi September 1996;21

(9):553–4, 576. Three compounds were isolated from the active fraction Lowering blood-lipid in the traditional Chinese beeswax (Apis cerana or A. mellifera). They were identified as dotriacontanol, triacontanol and octacosanol by chemical and spectroscopic methods.

Carbajal D, Molina V, Valdes S, Arruzazabala L, Rodeiro I, Mas R, Magraner J: Possible cytoprotective mechanism in rats of D-002, an anti-ulcerogenic product isolated from beeswax. J Pharm Pharmacol August 1996;48(8):858–60. D-002 is an anti-ulcerogenic product, isolated from beeswax, which consists of a well-defined mixture of higher primary aliphatic alcohols. It is highly effective against ethanolinduced ulcers. This study was designed to determine if D-002 shows cytoprotective properties on gastric mucosa in ethanol-induced ulcers. The involvement of endogenous prostaglandins in the protective effect of D-002 was also investigated. When a subulcerogenic dose of indomethacin (10 mg kg-1) was injected simultaneously with oral administration of ethanol, oral pre-treatment with D-002 (5–100 mg kg-1) partially inhibited the gastric protection. D-002 (5 and 25 mg kg-1) administered to normal rats significantly increased the soluble mucus content and also prevented its reduction in rats with ethanol-induced ulcers. In addition, D-002 administered at 5 and 25 mg kg-1 prevented the increase of vascular permeability induced by ethanol (60%) and reduced the concentration of thromboxane B2 (TXB2) in gastric mucosa of rats with ethanol-induced ulcers. These results support the hypothesis that the anti-ulcerogenic properties of D-002 could be related to a cytoprotective mechanism.

Dorset DL: The crystal structure of waxes. Acta Crystallogr B Dec. 1, 1995;51 (Pt 6): 1021–8. Quantitative electron crystallographic studies have been carried out on epitaxially oriented multi-component waxes. Intensities from two paraffin-based samples, an artificial six-component medium wax (equimolar distribution of chain lengths) and a petroleum-based wax (Gaussian distribution of chain lengths) have been used to determine their crystal structures. As found earlier for binary paraffin solid solutions, differences in molecular volume are compensated by longitudinal molecular shifts within individual lamellae. Nevertheless, each lamellar surface must remain flat enough, and with enough crystallographic order intact, to nucleate the next lamella, thus accounting for the observed long-range correlation in these crystals. Recrystallized beeswax also has a layer packing somewhat similar to the paraffin waxes. However, in this case, the lamellar order is 'frustrated' so that a certain amount of 'nematically' ordered material must be present, spanning the nascent lamellar interfaces.

Carbajal D, Molina V, Valdes S, Arruzazabala L, Mas R: Anti-ulcer activity of higher primary alcohols of beeswax. J Pharm Pharmacol September 1995;47(9):731–3. The anti-ulcer effects of a natural mixture of higher aliphatic primary alcohols, designated D-002, isolated from beeswax, were compared with those of cimetidine on indomethacin-, ethanol-, water-immersion-induced ulcers and on gastric secretion in rats. D-002 (25–50 mg kg-1 p.o.) was similar to cimetidine in dose-dependently reducing the duration of indomethacin-induced ulcers while also being effective in preventing ethanol-induced ulcers, which are not affected by cimetidine. On the other hand, D-002 (100 mg kg-1) moderately decreased the volume of gastric basal secretion in pylorus-ligated rats, but not the acidity. Nevertheless, it inhibited gastric ulcer induced by pylorus-ligation at doses (50 mg kg-1) that were ineffective in decreasing the volume. In addition, 100 mg kg-1 of D-002 prevented the formation of acute gastric ulcers induced in rats by waterimmersion stress. The results demonstrate the anti-ulcer activity of the preparation in different experimental models suggesting its potential value for ulcer therapy.

Zanoschi C, Ciobanu C, Verbuta A, Frincu D: The efficiency of some natural drugs in the treatment of burns. Rev Med Chir Soc Med Nat lasi January 1991–June 1995(1–2):63–5. In this paper we present an original product for burns. It is an ointment with bacteriostatic, bactericidal and epithelializing action and it is make up in accordance with technology of sunflower oil, beeswax, sintopholin, chloramphenicol, procaine, and vitamin E. An experimental study on burnt animals in order to prove the efficiency of the product was carried out. For histological investigation tegument was collected from the burnt area. A rapid evolution of epithelialization was found in case of treated animals as distinguished from control sample, where the infected crust was far from being healed. We also present some photos in account with the upper fact.

Ludianskii E A: The use of the products of bee raising in medicine. Feldsher Akush September 1989;54(9):36–9.

Blum M S, Jones T H, Rinderer T E, Sylvester H A: Oxygenated compounds in beeswax: identification and possible significance. Comp Biochem Physiol B 1988;91 (3):581–3.1. Beeswax synthesized by non-foraging honeybee workers contains six oxygenated volatiles in addition to a series of normal alkanes. 2. Decanal constitutes nearly 50% of the oxygenated volatiles and is accompanied by octanal, nonanal, furfural, benzaldehyde and 1-decanol. 3. The possible significance of the aldehydes as stimulators of hoarding behaviour and attractants for wax moths is discussed.

Chlorazak T, Szaflarski J, Seferowicz E, Scheller S: Preliminary evaluation of clinical usefulness of propolis (beeswax) preparations. Przegl Lek 1971;28 (12):828–31.

Olive oil used in the formulation provides several functions. It is an excellent emollient and through its many other components, complements the overall activity of the product. Olive Oil is a complex compound made of fatty acids, vitamins, volatile components, water-soluble components and microscopic bits of olive. Primary fatty acids are Oleic and linoleic acid. It also contains Vitamin E and carotene. Other constituents of olive oil include: phenols, free fatty acids, triacylglycerols, diacylglycerols, and monoacylglycerols, thiobarbituric acid, Pheophytin A andetc. The flavonoid polyphenols in olive oil are natural anti-oxidants, which have been shown to have a host of beneficial effects from healing sunburn to lowering cholesterol, blood pressure, and risk of coronary disease.There are as many as 5 mg of antioxidant polyphenols in every 10 grams of olive oil. Many other nut and seed oils have no polyphenols.

What is claimed is:

1. A pharmaceutical composition for the treatment of diaper rash consisting essentially of beeswax, olive oil, β-sitosterol and the herb Coptis chinensis Franch.

2. The pharmaceutical composition of claim 1 wherein the proportion of Coptis chinensis Franch represents about 5% of the total formulation added as an extract or decoction.

3. The pharmaceutical composition of claim 1 wherein soybean extract is used as a source of β-sitosterol.

4. The pharmaceutical composition of claim 1 wherein the concentration of β-sitosterol in the composition ranges between 0.1 to 50%.

5. The pharmaceutical composition of claim 1 wherein the composition is in a dosage form suitable for application to skin, said dosage form including ointment, cream, poultice, lotion, solution, spray, or bandage.

6. The pharmaceutical composition of claim 1 wherein olive oil is an emollient.

7. The pharmaceutical composition of claim 1 wherein beeswax is of natural variety.

8. The pharmaceutical composition of claim 1 wherein the quantity of beeswax comprises 2–20% of the composition.

9. The pharmaceutical composition of claim 1 wherein the quantity of beeswax comprises 8% of the composition.

10. The pharmaceutical composition of claim 1 wherein the concentration of β-sitosterol in the composition is about 0.5%.

* * * * *